Aug. 30, 1949. A. TOTH Plant Pat. 867
BARBERRY HEDGE PLANT
Filed Dec. 24, 1947
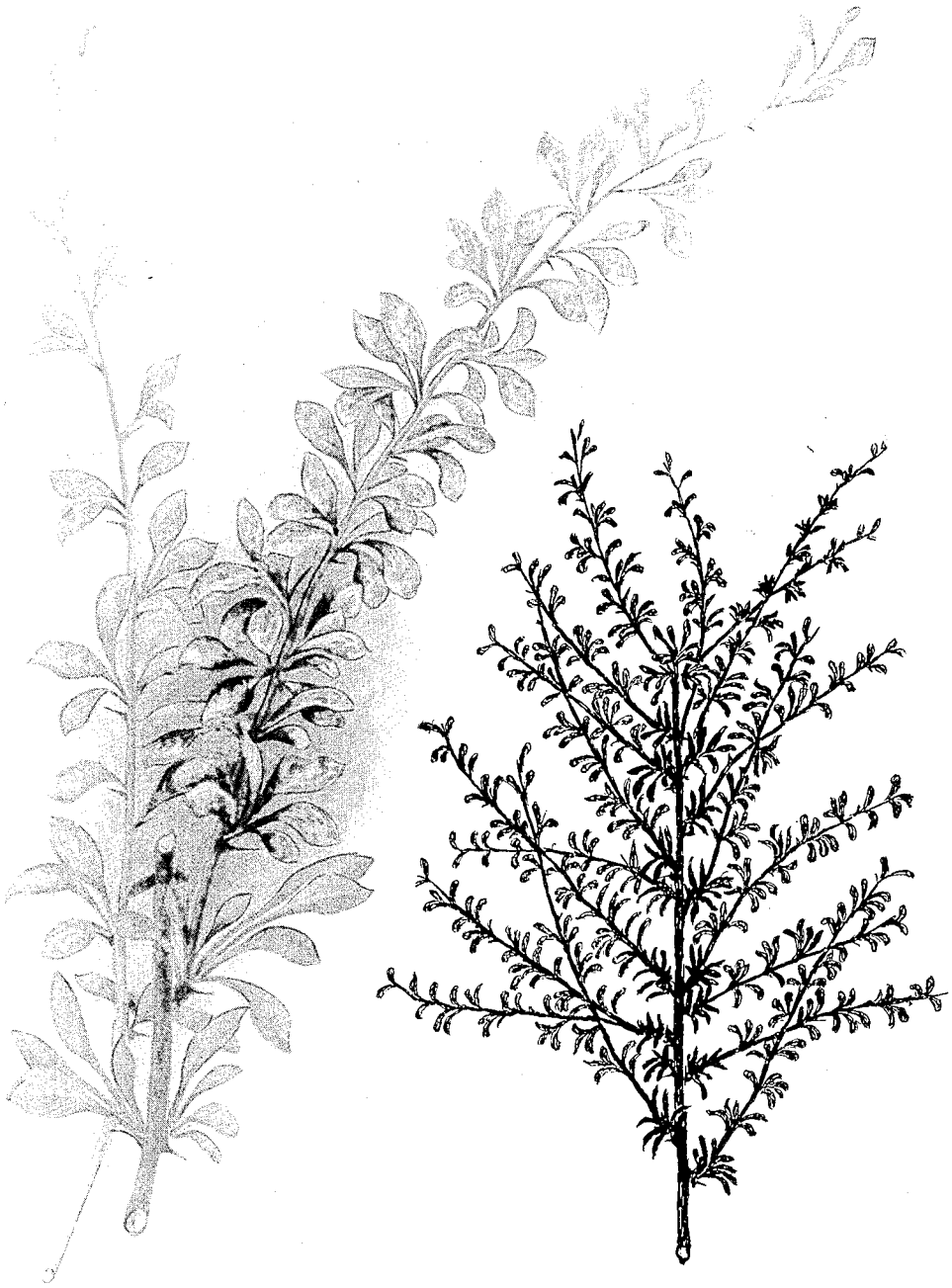
WITNESS
Addison F. Avery
INVENTOR
ALEX TOTH,
BY Justin E. Macklin
ATTY.

Patented Aug. 30, 1949

Plant Pat. 867

UNITED STATES PATENT OFFICE

867

BARBERRY HEDGE PLANT

Alex Toth, Madison, Ohio

Application December 24, 1947, Serial No. 793,625

1 Claim. (Cl. 47—59)

This invention relates to a novel and distinct variety of barberry hedge plant produced by crossing a Japanese barberry (Thunbergi) as the female parent with a male parent barberry which appeared as a visitor in about twenty thousand *Berberis thunbergi* plants. The male parent was an aberrant form.

This new hedge plant is a distinctly hardy variety. It grows without protection in the temperate regions.

The shrub may be asexually reproduced by first planting cuttings for rooting in a hot-bed in the summer of one year, and the following spring it may be set out on the ground, the growth at the end of the second summer being up to twelve to fifteen inches. At the end of the third summer growth has reached a height of from one and a half to two feet. Large numbers of these plants have thus been grown in Northern Ohio (in Lake County).

The foliage is thick and the stems and stalks are sturdy. The leaves are variegated in color, containing a predominance of green with pronounced areas or splotches, dots, and the like, of white, light gray, and yellow.

The stems range from pink and red to green on new foliage, while more mature stems or branches are reddish brown.

The distinctive colorings of the leaves of the plant according to the "Maerz and Paul Dictionary of Color" may be described as follows:

The mature leaf is mottled having its light green corresponding to Maerz and Paul Plate No. 21–E–3, the dark green on these leaves corresponding to Plate No. 23–J–5, and the back of the mature leaf corresponding to Plate No. 22–C–6.

The circle of leaves that radiate from the main stem at the base of the side branches, as shown in the drawing, it will be noted, are comparatively solid green, corresponding to Plate No. 22–L–7.

The new foliage appearing on the spray at the left of the drawing and having the mottling less pronounced has its darker green corresponding to plate No. 19–L–6 with lighter green corresponding to Plate No. 19–H–2.

The newest leaves at the upper part of the spray at the left are still lighter green, and portions of the new stem are red to pink in color.

The dark brown color of the main heavy stem, as shown, corresponds to Plate No. 56–E–1, while the reddish tinge of the side branch corresponds to Plate No. 7–H–10.

The colorful stems, particularly because of the reddish tinge, add a richness to the appearance of the shrub and lend a depth of color to a hedge of such shrubs.

The drawing illustrates many of the characteristics not found in the parent stock nor in any known varieties. These characteristics greatly add to the value of the plant as shrubs for hedges and increase its beauty.

The shrubs bear red berries as is characteristic of such barberry hedges, but which are not shown in the drawing.

Having now fully shown and described my new variety of barberry hedge plant and the mode of its production, what I claim and desire to secure by Letters Patent of the United States is:

The new and distinct variety of barberry hedge plant as described and illustrated, characterized by leaves variegated in color with predominance of green and pronounced areas of white, light gray and yellow, and having stems ranging from pink and red to green on new foliage and reddish brown on more mature stems, and further characterized by being hardy and sturdy.

ALEX TOTH.

No references cited.